(12) United States Patent
Lee et al.

(10) Patent No.: US 6,224,373 B1
(45) Date of Patent: May 1, 2001

(54) SIMULATION METHOD FOR VISUALIZING DENSITY OF JAWBONE FOR DENTAL IMPLANTATION

(75) Inventors: Yong-gu Lee, Sungnam; Youngmin Kim, Seoul, both of (KR)

(73) Assignee: Samsung SDS Co., Ltd., Seoul (KR)

( * ) Notice: Subject to any disclaimer, the term of this patent is extended or adjusted under 35 U.S.C. 154(b) by 0 days.

(21) Appl. No.: 09/416,147

(22) Filed: Oct. 11, 1999

(30) Foreign Application Priority Data

Mar. 15, 1999 (KR) .................................................. 99-8581

(51) Int. Cl.$^7$ ............................ A61C 13/12; A61C 19/04
(52) U.S. Cl. ............................ 433/172; 433/68; 433/215
(58) Field of Search ............................... 433/172, 29, 68, 433/215, 229, 173

(56) References Cited

U.S. PATENT DOCUMENTS

| | | | |
|---|---|---|---|
| 4,575,805 | * | 3/1986 | Moermann et al. ................... 433/68 |
| 5,320,529 | * | 6/1994 | Pompa ................................. 433/215 |
| 5,342,202 | * | 8/1994 | Deshayes ............................. 433/68 |
| 5,725,376 | * | 3/1998 | Poirier ................................. 433/172 |
| 6,049,743 | * | 4/2000 | Baba .................................... 433/172 |

FOREIGN PATENT DOCUMENTS

| | | |
|---|---|---|
| 0 180 482 A2 | 5/1986 | (EP) . |
| 0 180 482 A3 | 7/1988 | (EP) . |

OTHER PUBLICATIONS

Copy of European Search Report for Applicants' corresponding European Patent Application No. EP 99 30 7302 (three pages).

Seipel, et al., Oral implant treatment planning in a virtual reality environment, *Computer Methods and Programs in Biomedicine*, vol. 57, No. 1–2, 1998, pp. 95–103.

Rosenfeld and Mecall, Use of prosthesis generated computed tomographic information for diagnosis and surgical treatment planning, *Journal Of Esthetic Dentistry*, vol. 10, No. 3, 1998, pp. 132–148.

Jeffcoat, et al., Planning interactive implant treatment with 3–D computed tomography, *JADA*, vol. 122, 1998.

* cited by examiner

*Primary Examiner*—Todd E. Manahan
(74) *Attorney, Agent, or Firm*—Knobbe, Martens, Olson & Bear, LLP

(57) ABSTRACT

A simulation method and a computer readable medium therefor visualize in three dimensions the density of a jawbone at an implant area where an implant screw contacts the jawbone using information about the density of the jawbone obtained by computed tomography (CT) and a virtual implant screw. The simulation method includes the steps of forming a three-dimensional image of the jawbone, the image including information about the jawbone density. A color map corresponding to the density distribution of the jawbone is set, and a virtual implant screw is modeled by a plurality of brick elements. Then, the virtual implant screw is inserted into a surgical area of the jawbone image, and values of the jawbone density at the points where each brick element of the virtual implant screw contacts the jawbone, are calculated. Then, colors are searched in the color map corresponding to the density values of the jawbone image near each brick element, and faces of the virtual implant screw are colored. Using this invention, a dental surgeon can accurately ascertain the density of the jawbone at an implant area prior to actual implantation, thereby minimizing the side effects which may occur during actual implantation.

6 Claims, 9 Drawing Sheets

FIG. 7A
FIG. 7B
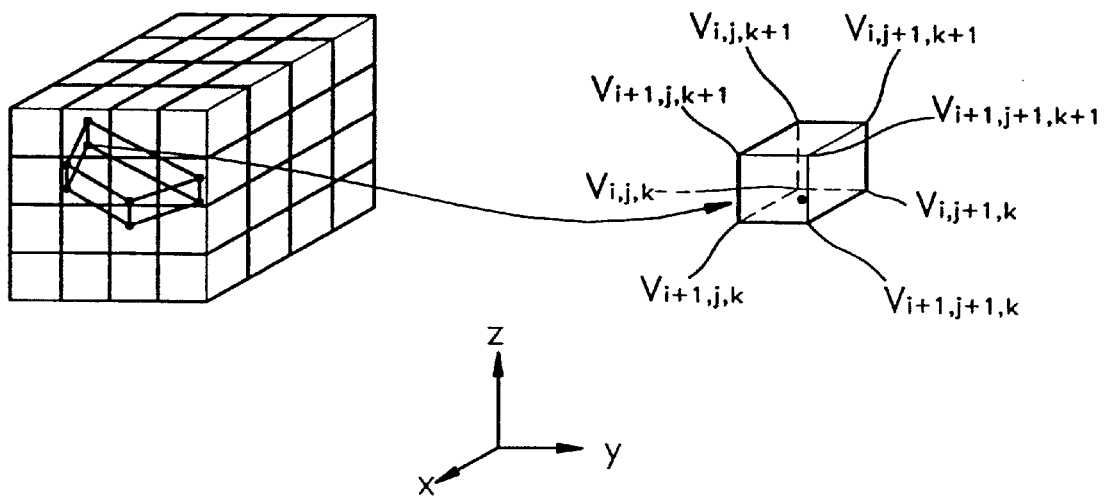
FIG. 7C
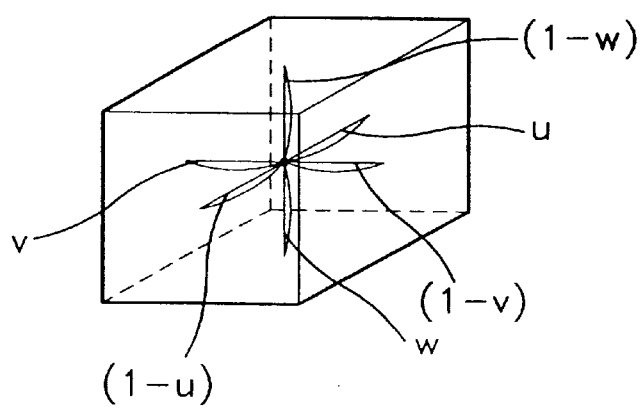

SIMULATION METHOD FOR VISUALIZING DENSITY OF JAWBONE FOR DENTAL IMPLANTATION

BACKGROUND OF THE INVENTION

1. Field of the Invention

The present invention relates to a simulation method for visualizing in three dimensions the density of a jawbone at the contact area between the jawbone and the surface of an implant screw using a virtual implant screw and based on information about the density of the jawbone obtained through computed tomography (CT) and also relates to a computer readable medium therefor.

2. Description of the Related Art

For the case where damage to teeth is too serious to repair, surgery for substituting artificial teeth for damaged teeth has become common. For such surgery, an implant screw for supporting the artificial teeth must be inserted into the jawbone.

FIGS. 1A through 1G illustrate each step of implantation. In detail, in the case where a tooth is damaged due to damage as shown in FIG. 1A, an artificial tooth is implanted into the damaged region as follows. The gum in the damaged region is cut as shown in FIG. 1B, a region into which an implant screw is to be inserted is drilled to form a hole as shown in FIG. 1C, and the implant screw is inserted into the hole as shown in FIG. 1D. Then, the implanted region is left to allow the implant screw to firmly bind, or osseointegrate, with the jawbone as shown in FIG. 1E. Usually, osseointegration takes about six months for the maxilla and about three months for the mandible. When the implant screw has firmly bound to the jawbone, the gum on the top of the implanted region is separated as shown in FIG. 1F and then an artificial tooth is mounted on the implant screw.

However, if a dentist fails to insert the implant screw into an appropriate region in an accurate direction during the above surgery, the implant screw cannot satisfactorily support the artificial tooth or the inappropriately inserted implant screw may encroach on alveolar nerves, causing numbness. Thus, the most important step in implantation is to accurately assess the density of the jawbone in the vicinity of a desired implantation location. In particular, contact between the implant screw and a low-density area and particularly encroachment on the nerves in the jawbone should be avoided.

Success in implantation depends on how accurately a dental surgeon knows the jawbone quality of a patient. The current leading method in accurately ascertaining the jawbone quality is computed tomography (CT). CT is a process by which an object is scanned by X-ray in many directions and synthesized through computation, resulting in an image of intersection. At a dental surgery, during CT scanning, either the maxilla or the mandible is typically scanned in 1.0-mm increments, resulting in about 45 image slices. FIG. 2 shows a three-dimensional reconstruction image of a mandible obtained by CT.

As shown in FIG. 2, the images provided by CT are at intersections perpendicular to the long axis of the cervical spine, and these images are not suitable for inspecting the contact area between the implant screw and the jawbone. This is why a reformatting technique is applied after the images have been scanned by CT. In general, the most prevalent reformatting orientation is coronal, or perpendicular to the ramus of the mandible, or jawbone. However, because the jawbone is arch-shaped, the actual reformatted images may not be parallel to each other. Also, images perpendicular to the jawbone as well as images perpendicular to the cervical spine are very helpful in examining an implant site. Unfortunately, images perpendicular to the jawbone do not display the density distribution of the jawbone in a three-dimensional view, so that an implant surgeon cannot fully observe the density of jawbone at the contact area between the implant screw and the jawbone.

Due to the complicated three-dimensional structure of the jawbone, it is difficult to accurately observe an implant site in the jawbone from only the intersection image perpendicular to the cervical spine. This is the reason why CT software for dentist's provides a function capable of viewing the jawbone at different angles. For example, as the most common function of the CT software, a user can obtain a vertical sectional image by only drawing a parabola on a desired region of a given intersection, the vertical image corresponding to the desired region. However, using only the planar intersection (tomographic) images in identifying the density of a jawbone having a three-dimensional structure is not suitable for precise implantation.

SUMMARY OF THE INVENTION

To solve the above problems, it is an object of the present invention to provide a simulation method for visualizing the density of a jawbone in three dimensions, at the contact area between an implant screw and the jawbone, for implantation of the implant screw for supporting an artificial tooth in the jawbone, and a computer readable medium for the simulation method.

According to an aspect of the present invention, there is provided a simulation method for visualizing the density of a jawbone at an implant area into which an implant screw for supporting an artificial tooth is inserted, comprising the steps of: (a) forming a three-dimensional image of the jawbone, the image including information about the jawbone density; (b) setting a color map corresponding to the density distribution of the jawbone; (c) modeling a virtual implant screw on a plurality of brick elements; (d) inserting the virtual implant screw into a surgical area of the jawbone image; (e) calculating values of the jawbone density at the points where each brick element of the virtual implant screw contacts the jawbone; and (f) searching for colors in the color map corresponding to the density values of each brick element, and coloring faces of the virtual implant screw.

The invention can also be embodied as computer readable code on a computer readable medium. The computer readable medium is any data storage device that can store data which can be thereafter be read by a computer system. Examples of the computer readable medium include read-only memory, random-access memory, CD-ROMs, magnetic tape, floppy disks, optical data storage devices. The computer readable medium can also be distributed over a network computer system so that the computer readable code is stored and executed in a distributed fashion.

According to another aspect of the present invention, there is provided a computer readable medium containing program instructions for visualizing the density of a jawbone at an implant area into which an implant screw for supporting an artificial tooth is inserted, the computer readable medium comprising: computer readable code for forming a three-dimensional image of the jawbone, the image including information about the jawbone density; computer readable code for setting a color map corresponding to the density distribution of the jawbone; computer readable code for modeling a virtual implant screw on a plurality of brick elements; computer readable code for inserting the virtual implant screw into a surgical area of the jawbone image; computer readable code for calculating values of the jawbone density at the points where each brick element of the virtual implant screw contacts the jawbone; and computer readable code for searching for colors in the color map corresponding to the adjacent density values of each brick element, and coloring faces of the virtual implant screw.

BRIEF DESCRIPTION OF THE DRAWINGS

The above object and advantages of the present invention will become more apparent by describing in detail preferred embodiments thereof with reference to the attached drawings in which:

FIGS. 7A, 7B and 7C illustrate the calculation of a CT number at a node of a brick element by the grid points of CT slices.

DESCRIPTION OF THE PREFERRED EMBODIMENTS

Computed tomography (CT), which can be used to diagnose the internal status of a damaged part of the body without surgery, gives CT numbers of a continuous three-dimensional object at a finite number of rectilinear grid points. Also, because the CT number, or Hounsfield unit, is directly proportional to the density of the object at the corresponding point, the CT numbers are a surrogate for the density of the object.

In a simulation method according to the present invention, the density of a jawbone at an implant area can be visualized in three dimensions from the information about the bone density obtained by the CT using a virtual implant screw which is modeled to have a similar shape to that of an actual implant screw and is inserted into the implant area. That is, the virtual implant screw, which is a three-dimensional computer representation of an implant screw, may be graphically positioned within the computer generated image (model) of the jawbone using computer-assisted motion and translation techniques known to those of skill in the art.

The main idea for such visualization is in positioning the virtual implant screw into an image obtained from CT slices, and coloring the surface of the screw according to density values. Here, coloring is performed by a predetermined color map which has been set corresponding to each CT number. Here, the simulation method can be simplified by modeling the virtual implant screw as brick elements and then coloring the brick elements. The details are as follows:

(1) the virtual implant screw is modeled as a mesh consisting of brick elements, (2) the virtual implant screw is positioned at a surgical area of the image obtained by CT, by the necessary translation and rotation, (3) density values (CT numbers) corresponding to each node of the brick elements are computed by a linear interpolation method, and (4) faces of brick elements, i.e., the surfaces of the virtual implant screw, are colored according to node values using a color map.

According to the present invention, a three-dimensional jawbone model is reconstructed from CT images of a patient and virtual implantation is tried on the three-dimensional jawbone model, such that the structural effect of real implantation, which depends on the location and orientation of a surgical area, can be evaluated in advance. The three-dimensional CT reconstruction of the jawbone and virtual implantation will now be described.

Figure 3:
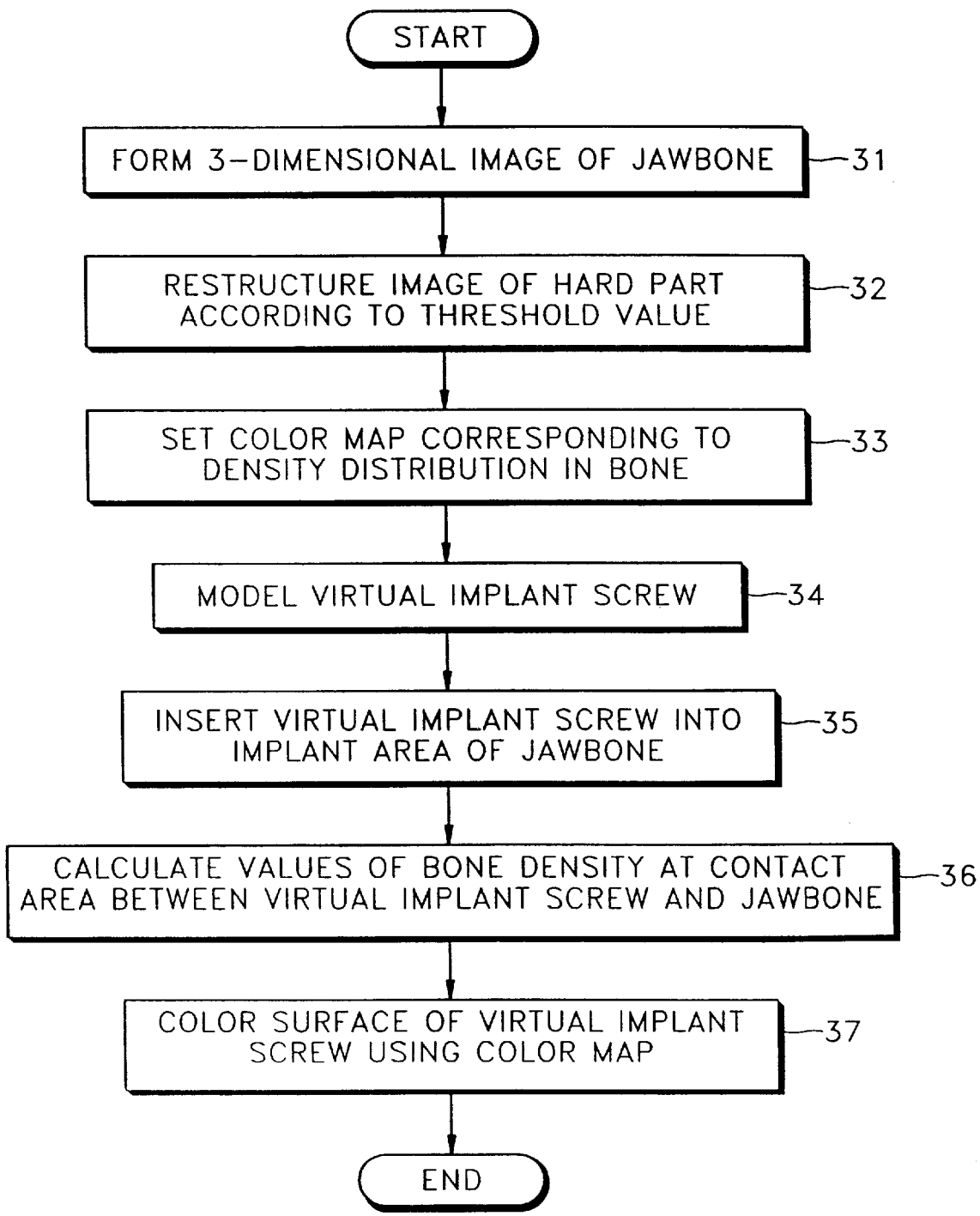
FIG. 3 is a flowchart of a simulation method for visualizing the density of a jawbone according to the present invention.

FIG. 3 is a flowchart illustrating a simulation method for visualizing the density of a jawbone according to the present invention.

Figure 1A:
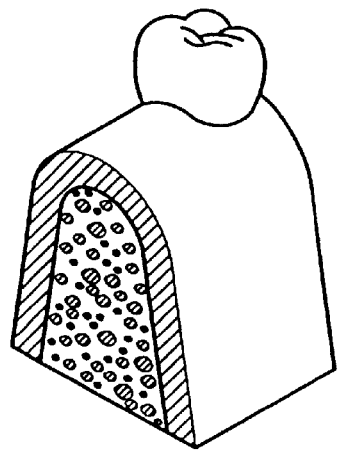
FIGS. 1A through 1G illustrate each step of dental implantation.
Figure 1B:
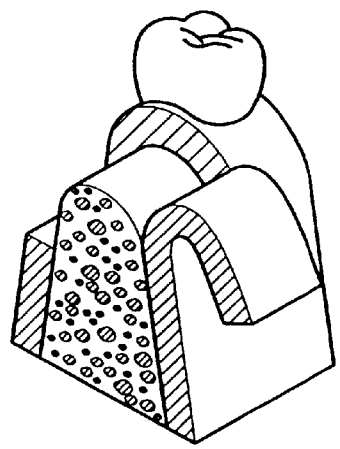
Figure 1C:
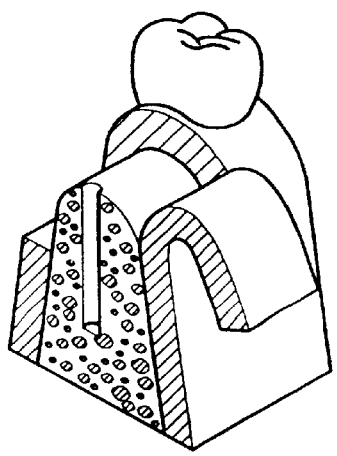
Figure 1D:
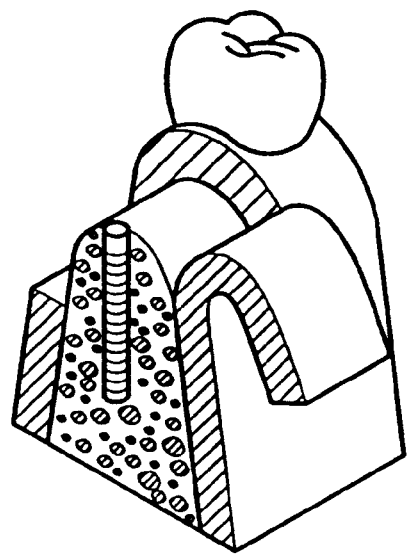
Figure 1E:
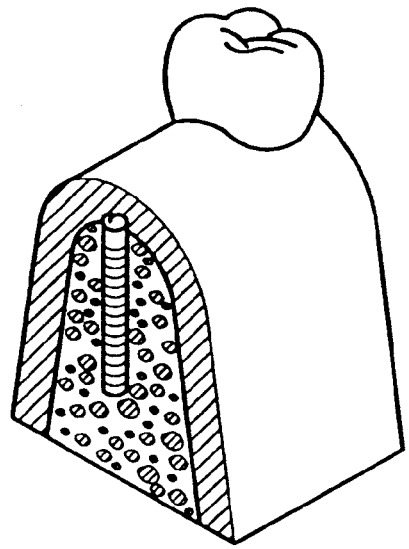
Figure 1F:
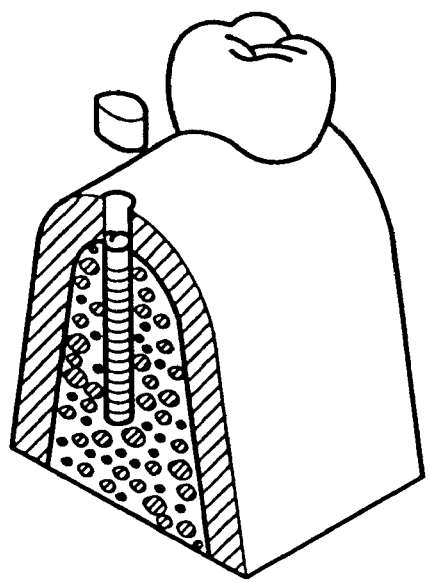
Figure 1G:
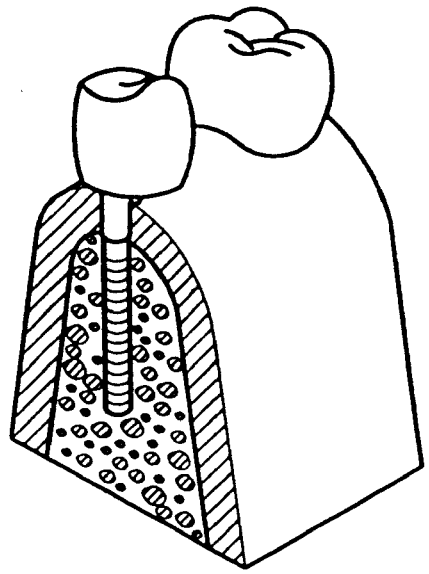
Figure 2:
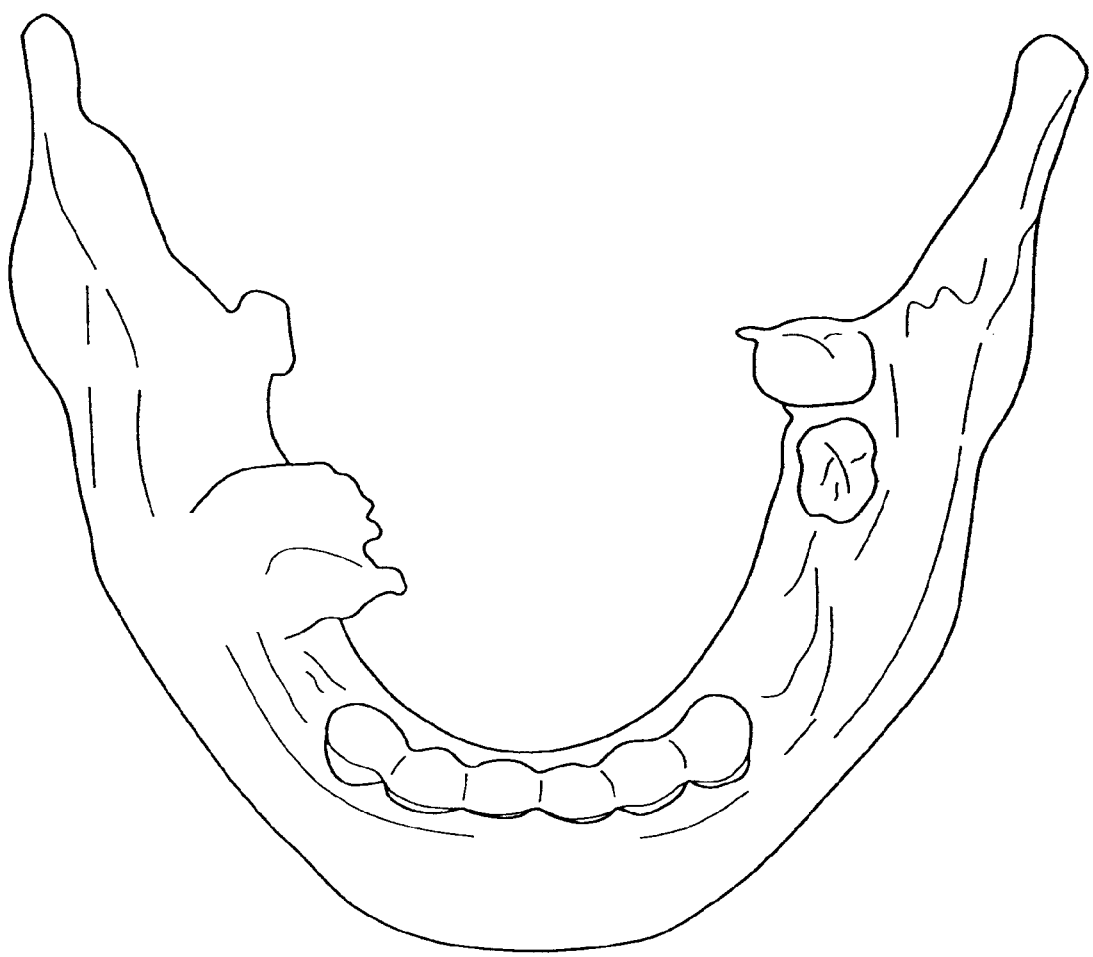
FIG. 2 shows a representation of a three-dimensional reconstruction image of a mandible obtained by computed tomography (CT)

A plurality of CT slices for a jawbone are obtained in the axial orientation, and a three-dimensional CT image of the jawbone, as shown in FIG. 2, is obtained using the CT slices. The CT number of each pixel in the CT slice ranges from 0 to $(2^N-1)$ (where N is the number of bits used to represent each pixel). If the number of bits is 16, the maximum CT number becomes 65,535. The jawbone image can be represented as a three-dimensional structure, including at an arbitrary angle, by stacking the CT slices and can also be reformed into an oblique cross-sectional image therefrom (step 31).

CT refers to a method in which X-rays are irradiated through an object at multiple predetermined angles, and the density at each point inside the object is calculated using the resulting plurality of data points which have been obtained by X-ray irradiation. In general, the X-rays are absorbed more in a high-density region than in a low-density region. A region of a CT image indicated by a relatively large CT number represents a high-density region such as bone. A region of a CT image indicated by a relatively small CT number represents a low-density region such as air, and a region indicated by an intermediate CT number generally represents a soft tissue of the human body or fluid density. Here, as the CT number becomes larger, the image is displayed in a brighter color or a different gray scale level on a cathode ray tube (CRT). A "threshold value" is used as a value for identifying a dense region of interest as distinct from an adjacent, less dense region, and all CT numbers smaller than the threshold value are set to zero or the minimum value. In this way, the image of only the dense region is distinctly contrasted from the remainder of the CT image, and a three-dimensional image of the jawbone can be reconstructed (step 32). Also, a user can appropriately select a threshold value by inspecting how the three-dimensional image of the dense region changes according to threshold values applied to the CT image.

In general, the CT slices are often annotated with various computer-added texts, for example, the slice number. However, such information, if displayed in the image field, can be removed during step 32. Because the intensity of these annotations is constant and is greater than that of the background intensity, the algorithm searches for pixels in the image having the largest intensity and then sets the intensity of all other, less dense pixels to zero or the minimum value. In this way, useless information can be removed.

The boundary between dense and less dense regions, for example, between healthy bone (dense) and infected or dead bone (less dense), can be distinguished by extracting CT numbers having a threshold value from a set of CT numbers for all slices. Here, the following operation may be performed in order to increase the processing speed of a computer.

When CT slices are stacked, a box-shaped image is obtained. Here, a small box region which a user is interested in can be defined rather than performing a computation for the entire image, which is called "data regioning". Also, the hard part of the jawbone may be displayed as separate anatomical parts or as a whole image by lowering the threshold value. Here, each piece of the dense part, which is separated from another, is called a "lump." In the present invention, only a required lump is selected and the selected lump is three-dimensionally reformed. Also, the reforming of lumps is performed two-dimensionally, rather than three-dimensionally, in order to reduce the amount of computation. That is, computation for 26 aneighboring pixels in three dimensions is simplified into the computation for 8 neighboring pixels in two dimensions. According to the simplified computation, the values of pixels located at the same position in each slice (pixels located on the same vertical axis when the CT slices are stacked) are summed, the image of a representative one CT slice is computed, and the computation of 8 neighboring pixels in two dimensions is performed. Here, the 26 neighboring pixels include the pixels located around the faces, the edges and the vertices with respect to a pixel, and the 8 neighboring pixels include the pixels located around the edges and vertices with respect to a pixel.

To simplify data processing, the following process may be performed. After analyzing the connectivity of the jawbone from the 26 neighboring pixels in three dimensions, lumps other than the largest lump may be erased, or an image of metal in the oral cavity, which causes interference to the CT image, may be automatically corrected to remove image artifacts. Also, in order to improve the display speed of a screen during real-time rendering, it is necessary to reduce the number of triangles the user intends to draw for the rendering. In particular, most triangles placed on the same plane are combined, resulting in a small number of triangles. Methods for reducing the number of triangles includes vertex-based decimation and edge-based decimation. In vertex-based decimation, triangles that share vertices are erased or averaged, so that a small number of large triangles are drawn in the resulting space. Meanwhile, in edge-based decimation, two triangles that share an edge are combined into one large triangle by erasing the shared edge.

Afterwards, a color map corresponding to the CT numbers, that is, the density distribution of the jawbone, is prepared (step 33). Blue, green and red are advantageously used. For example, in a particular embodiment, blue is assigned to the maximum CT number, red is assigned to the minimum CT number, and green is assigned to the CT number corresponding to the arithmetic average between the maximum and minimum CT numbers. This results in two spans, with one span between blue and green and the other span between green and red. If a CT number is given, the span corresponding to the CT number is determined, and the color of the CT number is determined by linearly interpolating two end colors of the corresponding span. By doing so, the density of the jawbone at an implant area where the virtual implant screw "contacts," or abuts, the jawbone image can be visualized in color as a three-dimensional image.

As used herein, the term "color map" refers to a graphical representation of CT density values as colors or gray scale levels. "Coloring" refers to assigning colors or gray scale values to particular CT density values. The density distribution of the jawbone may be displayed in a gray scale. The maximum density is set as black and the minimum density is set as white, and then linear interpolation is performed using the maximum and minimum density values such that a given density is displayed in a gray scale.

In the case where the CT number for each pixel of a CT is expressed with 16 bits, the number of cases in CT numbers is 65,536. Meanwhile, a general computer monitor can display only 256 brightness values in gray levels. Thus, displaying 65,536 CT numbers with 256 colors lowers discrimination of parts of the image. Even though 256 colors are not sufficient to display the CT images corresponding to all CT numbers, the distribution of CT numbers can be effectively expressed with 256 colors by delimiting only an area of interest in the dense part of the image.

Figure 4:
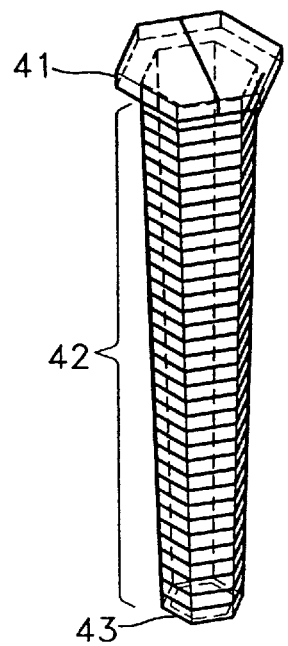
FIG. 4 shows a virtual implant screw used to identify the bone density at an implant area in the present invention.
Figure 5A:
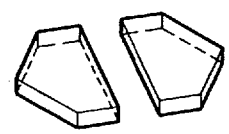
FIGS. 5A, 5B and 5C show basic shapes of brick elements consisting of the head, the rod and the end tip of the virtual implant screw shown in FIG. 4.
Figure 5B:
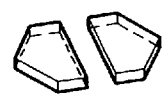
Figure 5C:

The virtual implant screw is modeled as brick elements in step 34. FIG. 4 shows an implant screw model used in order to identify the density of the jawbone at an implant area according to the present invention. FIGS. 5A, 5B and 5C show the basic shapes of the head, the rod and the end tip of the implant screw, respectively, as the brick elements of the implant screw model.

The virtual implant screw shown in FIG. 4 comprises three parts: a head 41, a rod 42 and an end tip 43, and is formed by sequentially stacking brick elements such as those shown in FIGS. 5A, 5B and 5C. The head 41 is modeled on a hexagon having a cross-section which is larger than that of the rod 42, the rod 42 has a similar shape to the head 41, but is longer than the head 41, and the end tip 43 is also modeled on a hexagon having tapered sides. Here, the virtual implant screw is modeled to a shape which is nearly the same as that of a typical implant screw used in actual implantation. However, the virtual implant screw may be modeled in more detail if required. Also, modeling of the virtual implant screw depends on the resolution of a CT scanner, so that it is impractical to model a virtual implant screw more precisely than the resolution of the CT scanner.

Figure 6:
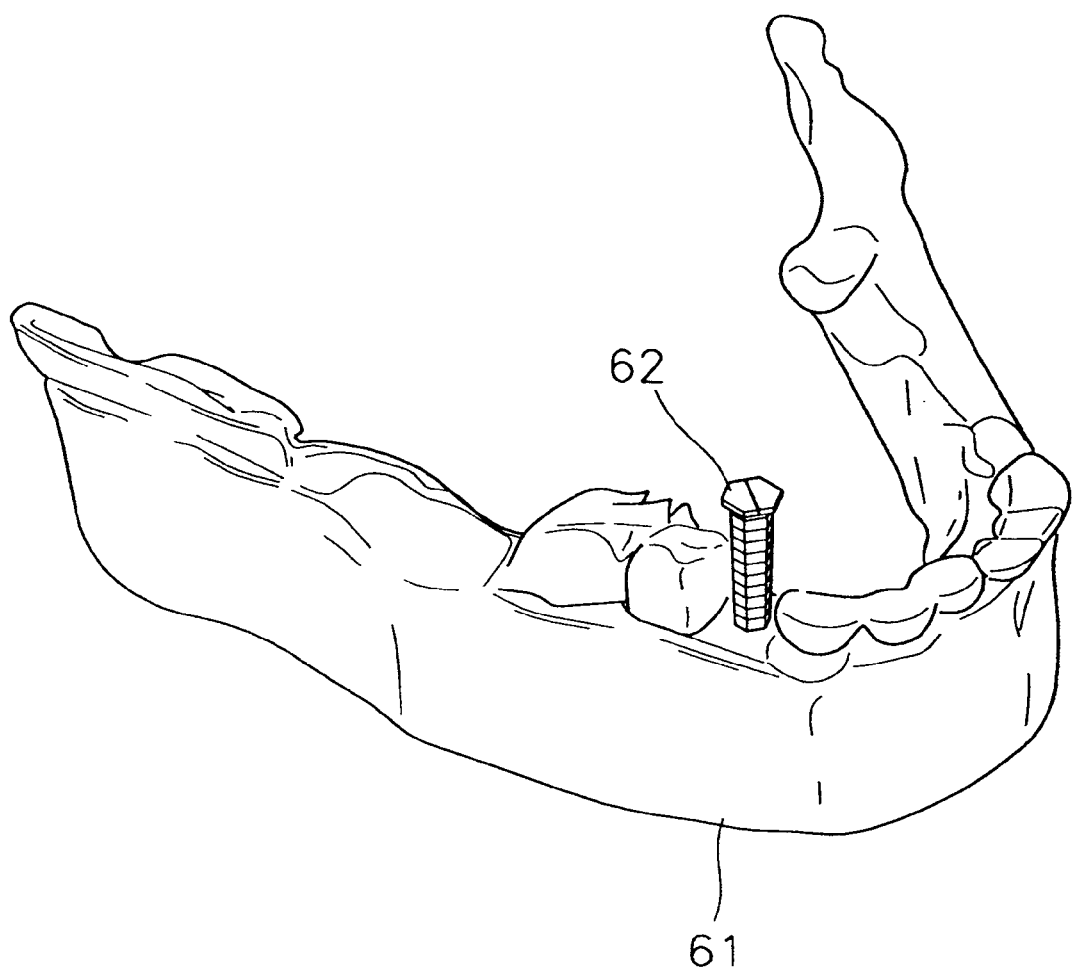
FIG. 6 illustrates the state where the virtual screw implant is inserted into an implant area of a mandible.

In step 35, the implant screw model is inserted into an implant area of a jawbone image. FIG. 6 shows the state where the virtual implant screw 62 is inserted into an implant area of the image of the jawbone image 61 obtained through CT. A dental surgeon can arbitrarily determine the location, orientation and depth of the virtual implant screw to be inserted.

In step 36, the CT numbers corresponding to nodes of each brick element of the virtual implant screw inserted into the CT image of the jawbone are computed. FIGS. 7A through 7C illustrate the calculation of CT numbers corresponding to each node of the brick element in relation to the grid points of CT slices. In general, the CT numbers are only defined on the grid points of the CT slices and the nodes of the brick element do not coincide with the grid points. Thus, the value of a node may be calculated by interpolating CT numbers at the grid points. Assuming that a node exists in a hexahedron as shown in FIG. 7B, the location of the node is expressed as a relative position with respect to the neighboring grid points shown in FIG. 7C, using u, v and w, which are distances from the node to the faces of the grid in x, y and z-axis directions. The value $V_N$ of the node is calculated by the following mathematical relation (1).

$$V_N = (1-u)(1-v)(1-w)V_{i,j,k} + (1-u)v(1-w)V_{i,j+1,k} + \quad (1)$$
$$u(1-v)(1-w)V_{i+1,j,k} + uv(1-w)V_{i+1,j+1,k} +$$
$$(1-u)(1-v)wV_{i,j,k+1} + (1-u)vwV_{i,j+1,k+1} +$$
$$u(1-v)wV_{i+1,j,k+1} + uvwV_{i+1,j+1,k+1}$$

After the CT values of eight nodes of the brick element are calculated, colors corresponding to the values are selected from a color map table, and the sides of the brick element are colored.

Figure 8:
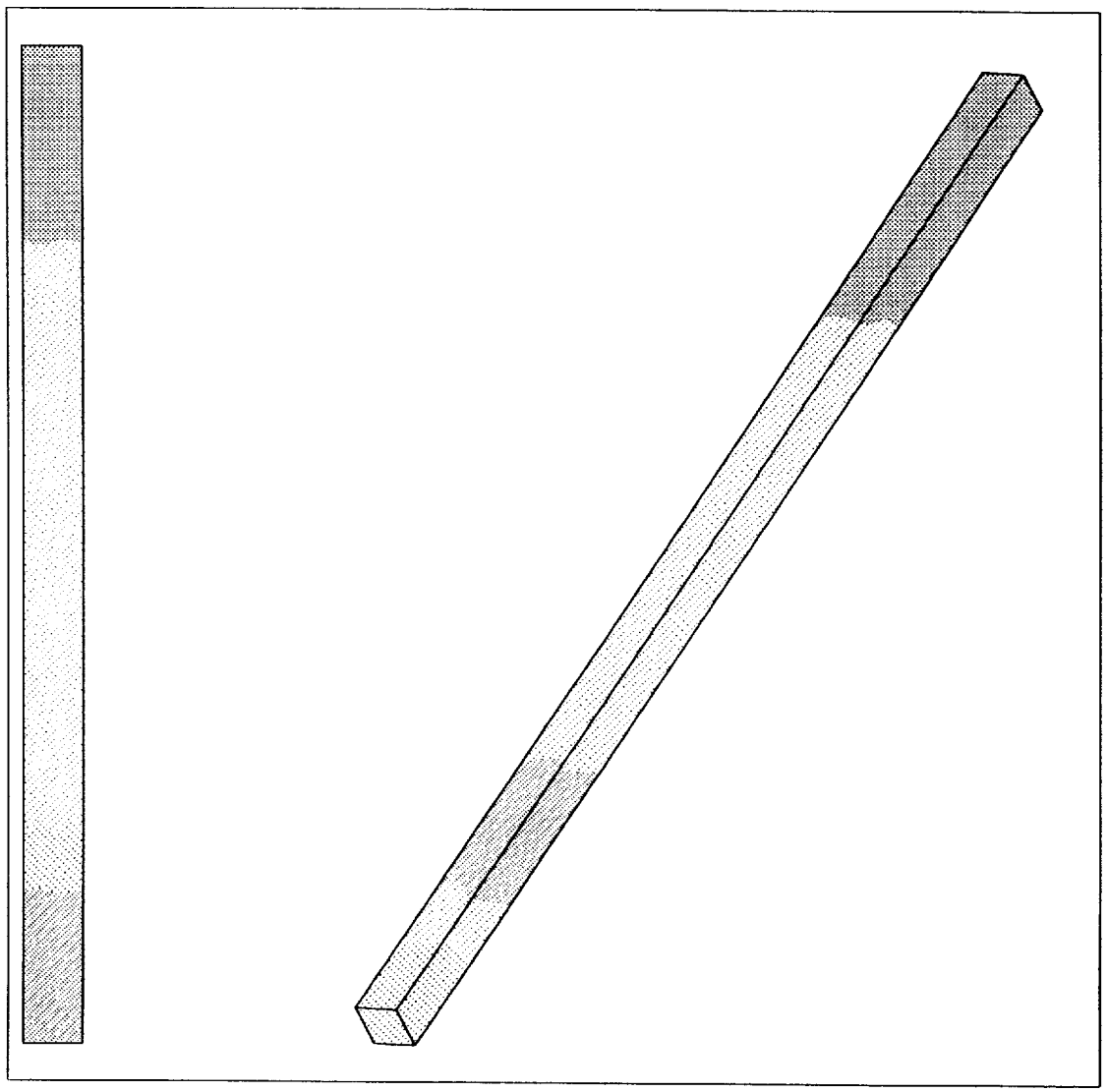
FIG. 8 shows a virtual implant screw which is colored according to the CT numbers.

In step 37, the entire implant screw is colored according to the CT values of each node of the brick elements with reference to the color map table. That is, the sides of each brick element contained in the implant screw are colored in different colors according to the CT values. FIG. 8 shows the virtual implant screw having brick elements which are depicted in gray scale according to the density of the jawbone. The bar located at the left of FIG. 8 represents the relation between the bone density and colors, or gray scale, and the virtual implant screw located at the right represents the simulation result. In FIG. 8, the bar is represented as a gray scale image. However, the bar may be displayed with real colors, using red, green and blue, for example, in actual application.

As shown in FIG. 8, the density distribution of a jawbone image at the implant area where the virtual implant screw and the jawbone image "contact" can be visualized by coloring the surface of the virtual implant screw, according to the location, orientation and depth of the implant screw. Thus, it can be determined whether the density of a jawbone is high enough for implantation. In particular, a high density of a jawbone around the implant area represents healthy bone and is important for strong binding of the implant screw with a jawbone.

The invention can also be embodied as computer readable code on a computer readable medium. The computer readable medium is any data storage device that can store data which can be thereafter be read by a computer system. Examples of the computer readable medium include read-only memory, random-access memory, CD-ROMs, magnetic tape, floppy disks, optical data storage devices. The computer readable medium can also be distributed over a network coupled computer systems so that the computer readable code is stored and executed in a distributed fashion.

As described above, in the simulation method for visualizing the density of a jawbone according to the present invention, a virtual implant screw modeled as brick elements is inserted into the image of a jawbone, obtained by CT, and the bone density at the area where the virtual implant screw contacts the jawbone is calculated. Then, the virtual implant screw is colored with different colors, or depicted in gray scale, according to the bone density, thereby visualizing the density of the jawbone at the implant area in three dimensions. Accordingly, a dental surgeon can accurately ascertain the density of jawbone at an implant area, thereby minimizing possible side effects in actual implantation.

What is claimed is:

1. A simulation method for visualizing the density of a jawbone at an implant area into which an implant screw for supporting an artificial tooth is inserted, comprising the steps of:

(a) forming a three-dimensional image of the jawbone, the image including information about the jawbone density;

(b) setting a color map corresponding to the density distribution of the jawbone image;

(c) modeling a virtual implant screw on a plurality of brick elements;

(d) graphically inserting the virtual implant screw into a surgical area of the jawbone image;

(e) calculating values of the jawbone density at the points where each brick element of the virtual implant screw abuts the jawbone image; and (f) searching for colors in the color map corresponding to the density values of the jawbone image at points adjacent to each brick element, and coloring faces of the virtual implant screw with said colors.

2. The simulation method of claim 1, wherein in the step (c) of modeling the virtual implant screw, the virtual implant screw comprises a head modeled as a protruded hexagonal shape, a rod modeled as a hexagonal shape longer than the head, and an end tip modeled as a hexagonal shape having tapered sides.

3. The simulation method of claim 1, further comprising the step of reforming the image of the jawbone by extracting an image of a region having a density higher than a predetermined threshold value.

4. The simulation method of claim 1, wherein in the step (b) of setting the color map, blue is assigned to the maximum value of bone density, red is assigned to the minimum value of bone density, and green is assigned to the value of bone density corresponding to the arithmetic average between the maximum and minimum values of bone density; two spans are formed, one between blue and green and the other between green and red; and the color of a specific value of bone density is determined by linearly interpolating two end colors of the corresponding span.

5. The simulation method of claim 1, wherein in the step (b) of setting the color map, the color map is set as a gray scale varying in sequence from the maximum value of bone density to the minimum value of bone density.

6. A computer readable medium containing program instructions for visualizing the density of a jawbone at an implant area, the computer readable medium comprising:

computer readable code for forming a three-dimensional image of the jawbone, the image including information about the density of the jawbone;

computer readable code for setting a color map corresponding to the density distribution of the jawbone;

computer readable code for modeling a virtual implant screw having a plurality of brick elements;

computer readable code for inserting the virtual implant screw into a surgical area of the jawbone image;

computer readable code for calculating values of the jawbone density at the points where each brick element of the virtual implant screw abuts the jawbone image; and computer readable code for searching for colors in the color map corresponding to the density values of the jawbone image at points adjacent to each brick element, and coloring faces of the virtual implant screw.

* * * * *